US011883572B2

(12) United States Patent
Irrgang et al.

(10) Patent No.: US 11,883,572 B2
(45) Date of Patent: Jan. 30, 2024

(54) DIALYSIS MACHINE AND METHOD OF OPERATING A DIALYSIS MACHINE

(71) Applicant: Fresenius Medical Care Deutschland GmbH, Bad Homburg (DE)

(72) Inventors: Tobias Irrgang, Aubstadt (DE); Tilman Stäblein, Würzburg (DE); Alfred Gagel, Litzendorf (DE); Peter Klöffel, Nüdlingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 432 days.

(21) Appl. No.: 17/042,271

(22) PCT Filed: Mar. 26, 2019

(86) PCT No.: PCT/EP2019/057609
§ 371 (c)(1),
(2) Date: Sep. 28, 2020

(87) PCT Pub. No.: WO2019/185638
PCT Pub. Date: Oct. 3, 2019

(65) Prior Publication Data
US 2021/0138134 A1 May 13, 2021

(30) Foreign Application Priority Data
Mar. 29, 2018 (DE) .......................... 102018107627.4

(51) Int. Cl.
*A61M 1/16* (2006.01)
(52) U.S. Cl.
CPC ........ *A61M 1/1656* (2013.01); *A61M 1/1603* (2014.02); *A61M 1/168* (2013.01); *A61M 2205/3317* (2013.01)

(58) Field of Classification Search
CPC .. A61M 1/1603; A61M 1/1656; A61M 1/168; A61M 2205/3317
See application file for complete search history.

(56) References Cited

U.S. PATENT DOCUMENTS

| 5,295,505 A | 3/1994 | Polaschegg et al. |
| 5,318,750 A | 6/1994 | Lascombes |

(Continued)

FOREIGN PATENT DOCUMENTS

| WO | WO93/09822 | 5/1993 |
| WO | WO94/11093 | 5/1994 |

(Continued)

OTHER PUBLICATIONS https://de.wikipedia.org/wiki/Leitfähigkeitsmessgerät—"Conductivity meter" Wikipedia article.

*Primary Examiner* — Dirk R Bass
(74) *Attorney, Agent, or Firm* — Jacobson Holman PLLC

(57) ABSTRACT

The present invention relates to a dialysis machine that is configured to be equipped with an extracorporeal blood system comprising a dialysis solution system that is configured to be equipped with a dialyzer, wherein a mixing region, in particular a mixing chamber, is provided in which the fresh dialysis solution or a component thereof is located in the operation of the dialysis machine, with a concentrate line being in fluid communication with the mixing region, through which concentrate line concentrate can be conducted from a concentrate container into the mixing region, wherein at least two electrically conductive elements are arranged spaced apart from one another in or at the concentrate line or lines; that a measuring device is provided which is electrically connected to the conductive elements and which is configured to measure the conductance or a value correlated therewith between them; and that a control unit is (Continued)

Figure 1:
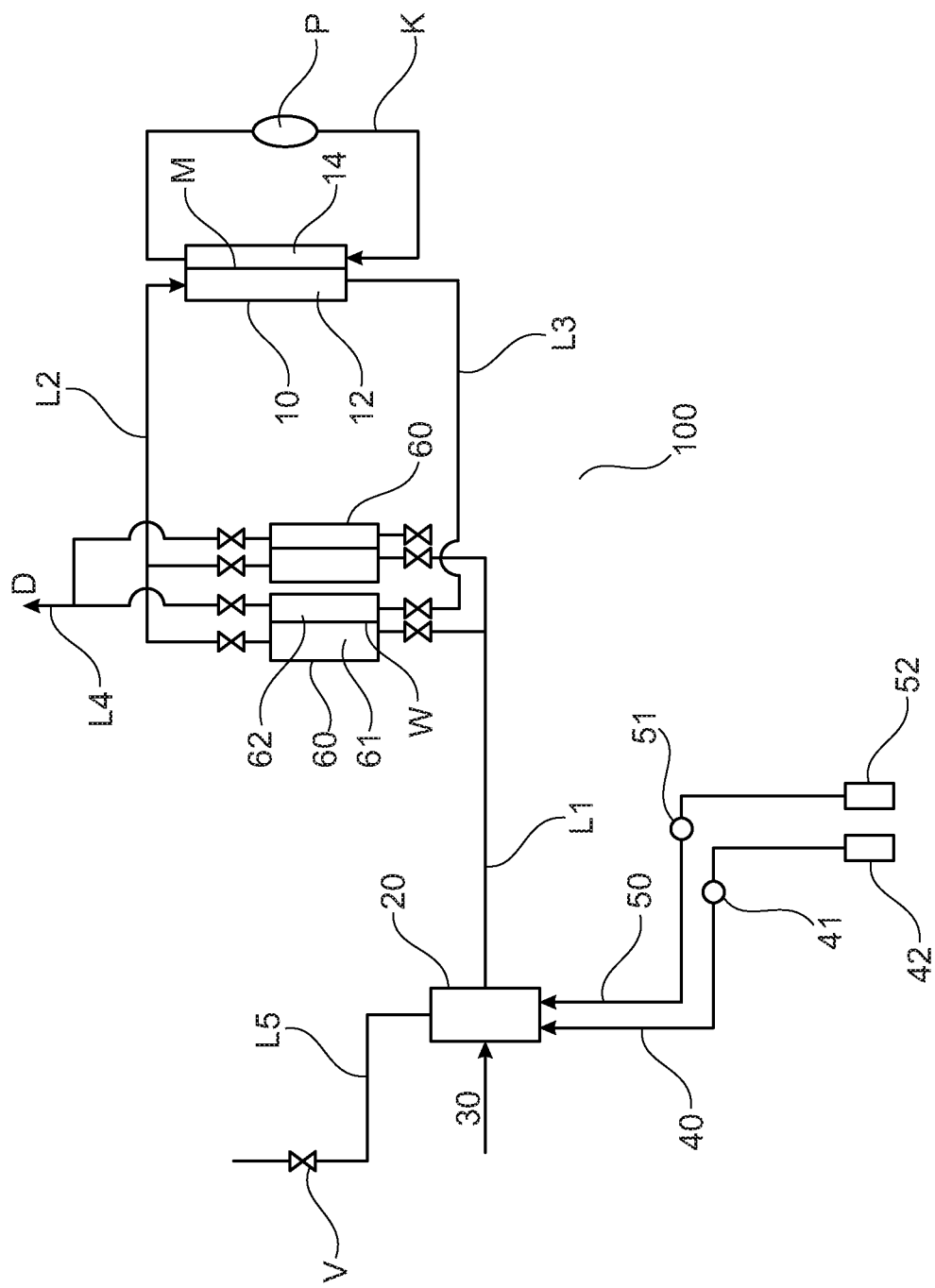

provided which is configured to compare the measured value with a desired value, with a limit value, or with a desired value range.

15 Claims, 3 Drawing Sheets

(56) References Cited

U.S. PATENT DOCUMENTS

2002/0088752 A1  7/2002  Balschat et al.
2016/0101225 A1  4/2016  Smith et al.

FOREIGN PATENT DOCUMENTS

| WO | WO2009/015882 | 2/2009 |
| WO | WO2010/146342 | 12/2010 |
| WO | WO2018/086739 | 5/2018 |
| WO | WO2018/208498 | 11/2018 |

DIALYSIS MACHINE AND METHOD OF OPERATING A DIALYSIS MACHINE

The invention relates to a dialysis machine that is configured to be equipped with an extracorporeal blood system comprising a dialysis solution system that is configured to be equipped with a dialyzer, wherein a mixing region, in particular a mixing chamber, is provided in which the fresh dialysis solution or a component thereof is located in the operation of the dialysis machine, with a concentrate line being in fluid communication with the mixing region, through which concentrate line concentrate can be conducted from a concentrate container into the mixing region.

The invention furthermore relates to a method of operating such a dialysis machine.

Dialysis machines of the initially named kind are known from the prior art. They are used within the course of a dialysis treatment to remove urea and other substances from the blood of a patient having no or reduced renal activity. The dialyzer of a dialysis machine is a filter unit having a blood chamber and a dialysis solution chamber that are separated from one another by a semipermeable membrane. The substances to be removed from the blood pass through the semipermeable membrane from the blood chamber into the dialysis solution chamber in the dialyzer.

A so-called balancing chamber is typically used for the purpose of balancing the quantity of dialysis solution supplied to the dialyzer and drained therefrom. Said balancing chamber has two balancing chamber halves which are separated from one another by a movable wall, which each have an inlet and an outlet and which can be opened and closed via a respective valve. While one of the balancing chamber halves is filled by fresh dialysis solution, the wall moves away from the filling balancing chamber half and in this manner displaces the consumed dialysis solution located in the other balancing chamber half. Since both balancing chamber halves are located in the same balancing chamber having fixed walls, the fed volume of fresh dialysis solution corresponds to the drained volume of consumed dialysis solution.

It is already pointed out at this point that the dialysis machine in accordance with the present invention can have such a balancing chamber system, but does not necessarily have to do so; it is thus a preferred, but nevertheless optional, feature. The at least one balancing chamber is thus an optional component of the dialysis machine. Alternatively to the use of one or more balancing chambers, the use of flow sensors with pumps for the balancing, which is e.g. also covered by the invention, is also possible, for example.

There is generally the possibility of supplying dialysis machines with a ready-to-use dialysis solution that is e.g. provided in a container or in a supply line.

It is equally known from the prior art to prepare the ready-to-use dialysis solution at the dialysis machine itself, with typically a plurality of concentrates being mixed with RO water in a mixing region. These concentrates are conveyed from concentrate containers by means of concentrate pumps to the mixing region that is preferably designed as a mixing chamber. In this respect, two concentrate containers are typically used of which one contains a base concentrate and the other an acid concentrate. The mixture obtained in this manner represents the ready-to-use dialysis solution and is then conveyed to the balancing chamber and is conducted from there to the dialyzer.

A known dialysis machine that is configured to be equipped with an extracorporeal blood system is shown schematically in FIG. 1.

The patient P is connected via the extracorporeal blood circuit K to the dialyzer 10 that has a blood-side compartment 14 and a dialyzate compartment 12 which are separated from one another by a semipermeable membrane M. The blood of the patient is preferably conducted in counter flow to the dialysis solution through the dialyzer 10 as is indicated by arrows that reproduce the flow direction.

The hydraulic system of the dialysis machine, i.e. the dialysis solution system, is generally designated by the reference numeral 100.

The dialysis solution is prepared in the mixing chamber 20 from the fluid, preferably RO water (RO=reverse osmosis), flowing in through the line 30 and from the two concentrates that flow into the mixing chamber 20 through the lines 40, 50. The conveying of the concentrates takes place by means of the pumps 41, 51 that convey the concentrate from the concentrate containers 42, 52.

The line L5 arranged at the mixing chamber 20 serves the venting of the dialysis solution and is closable by the valve V.

The balancing chamber 60 has the above-named balancing chamber halves 61 and 62 that are separated by the movable wall W that is not permeable for dialysis solution.

To ensure a continuous flow, two balancing chambers 60 connected in parallel are provided such as can be seen from FIG. 1. They can have an identical structure. The balancing chambers are shown simplified in that their inner walls are preferably shaped such that the wall W can lie completely at them in their extreme positions.

Each balancing chamber half 61, 62 of a balancing chamber 60 has a valve at the inlet side and at the outlet side to control the inflow and outflow into and out of the balancing chamber halves.

The two balancing chamber halves 61 of the balancing chambers 60 shown at the left serve the reception of fresh dialysis solution from the line L1. The dialysis solution moves from the balancing chamber halves 61 via the line L2 into the dialyzate-side compartment 12 of the dialyzer 10. The two balancing chamber halves 62 of the balancing chambers 60 shown at the right serve the reception of consumed dialysis solution that moves via the line L3 from the dialyzer 10 to the balancing chamber halves 62 and that is led after the balancing chamber via the line L4 to a drain (D).

If one or both of the concentrate containers 42, 52 are emptied, the case can occur that air moves into the balancing chamber or into another balancing system, which results in a balancing error since the affected balancing chamber half of the balancing chamber or a pump for a balancing conveying of the solution is then not completely filled with fresh dialysis solution, but in part with air, and thus less fresh dialysis solution is conveyed to the dialyzer than assumed. In these cases, air is conveyed or entrained via the concentrate lines into the mixing chamber and from there into the balancing chamber or into another balancing system.

This entrainment of air takes place e.g. by the opening of the venting valve V at the dead time of the balancing chamber. The dead time of the balancing chamber is to be understood as the time period in which the wall W is located in an extreme position (deflection fully to the right or to the left) and all the valves of the balancing chamber are closed. This state can, for example, last 100 ms.

Figure 2:
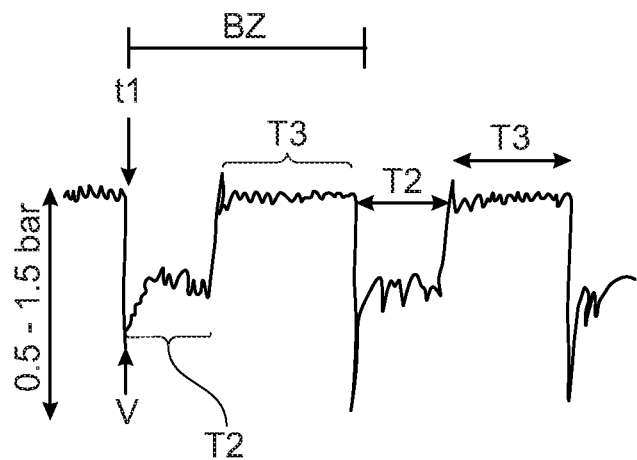

FIG. 2 shows the pressure development over time during a balancing chamber cycle, with the time t1 marking the named dead time. As marked by an arrow V in FIG. 2, the valve V is briefly opened at this time t1. The valve V is subsequently closed and the inflow valve of the balancing chamber is opened so that the pressure in the filling balancing chamber half 61 increases. This filling phase is marked by T2 in FIG. 2. In the subsequent state T3, the balancing chamber half is completely filled, which is also called the high-pressure phase of the balancing chamber.

The reference symbol BZ designates the total balancing chamber half cycle that covers all these phases or times.

The air rises upward in the lines 40, 50 with an open valve V1 and is then entrained into the balancing chamber or balancing chamber half 61 by the filling flow by means of which the balancing chamber 61 is filled. This produces an incorrect balance.

It is therefore the underlying object of the present invention to further develop a dialysis machine that is configured to be equipped with an extracorporeal blood system to the extent that the probability for an air entry into the dialysis solution or into a balancing system of the dialysis machine is reduced with respect to known dialysis machines.

This object is achieved by a dialysis machine that is configured to be equipped with an extracorporeal blood system comprising a dialysis solution system that is configured to be equipped with a dialyzer, wherein a mixing region, in particular a mixing chamber, is provided in which the fresh dialysis solution or a component thereof is located in the operation of the dialysis machine, with a concentrate line being in fluid communication with the mixing region, through which concentrate line concentrate can be conducted from a concentrate container into the mixing region, characterized in that at least two electrically conductive elements are arranged spaced apart from one another in or at the concentrate line or lines; that a measuring device is provided which is electrically connected to the conductive elements and which is configured to measure the conductance or a value correlated therewith between them; and that a control unit is provided which is configured to compare the measured value with a desired value, with a limit value, or with a desired value range.

The at least two conductive elements can here be arranged in or at the same concentrate line and/or in or at different concentrate lines.

It is conceivable that exactly one electrically conductive element is respectively arranged in or at a concentrate line and/or that one or more concentrate lines are provided in or at which a plurality of electrically conductive elements are arranged. An embodiment is thus conceivable in which one (or more) concentrate lines are each provided with at least two electrically conductive elements. Provision can alternatively or additionally be made that two or n (n>2) concentrate lines having a total of two or n (n>2) electrically conductive elements are present, that is, one electrical conductive element is provided per concentrate line.

The measurement takes place between the two electrically conductive elements, independently of whether they are in one and the same concentrate line or in different concentrate lines.

The electrically conductive element(s) can be designed as electrodes.

An arrangement is conceivable in which a respective one or at least one electrically conductive element is arranged in two concentrate lines and that the two concentrate lines form, together with the mixing chamber or another mixing region, a conductive path via which a signal (e.g. the conductance or a value correlated therewith) from the electrically conductive element of a concentrate line to the electrically conductive element of the other concentrate line can be measured. One concentrate line can, for example, be the line for the acid concentrate and the other concentrate line can be the line for the base concentrate. This signal is interrupted when one or both concentrate containers are empty or when air or an air-concentrate mixture is conveyed through the concentrate lines.

The concentrate lines are preferably configured as tubes.

The conductance, i.e. the reciprocal of the ohmic resistance or a value correlated therewith such as the voltage, the current, the ohmic resistance, etc. is thus measured, with the measurement taking place between the two electrically conductive elements.

If the concentrate is in the concentrate line, i.e. in the infeed, the electrical circuit is closed and a high conductance results. If air passes through the concentrate line, the conductance drops. If the conductance falls below a limit value, i.e. if it moves out of a desired value range, the presence of air can be recognized and an alarm can be triggered, for example.

The electrically conductive elements can, for example, be formed by hose connections that are arranged spaced apart from one another in the longitudinal direction of the concentrate line.

The electrically conductive elements are arranged at or in the concentrate line or lines such that they come into contact with the content of the concentrate line, i.e. with the concentrate, air, etc.

The electrically conductive elements preferably consist of metal, preferably of stainless steel and/or titanium.

A concentrate pump is preferably located in or at the concentrate line, with the conductive elements preferably being located upstream of the concentrate pump in the direction of flow of the concentrate to avoid a deteriorated recognition of air such as is present downstream of the concentrate pump. The case is generally also covered by the invention that the conductive elements are located downstream of the concentrate pump in the direction of flow of the concentrate.

The control unit is preferably configured to initiate an alarm and/or a special operating mode of the dialysis machine when the measured value (conductance or a value correlated therewith) does not agree with the desired value, exceeds or falls below a limit value, or is not in a desired value range. This is in particular the case, as stated above, when air or an air-concentrate mixture and not a pure concentrate is located in the region of the concentrate line between the electrically conductive elements.

The control unit or its recognition logic is preferably adapted to a specific distance of the two conductive elements from one another. If the distance between the conductive elements is changed, it may be necessary also to correspondingly adapt the recognition logic of the control unit.

In a further embodiment of the invention, the control unit is configured such that the alarm and/or the special operating mode of the dialysis machine is only initiated when the measured value does not agree with the desired value or exceeds or falls below a limit value or is not in a desired value range in each case more frequently than a threshold value.

If the dialysis machine has a balancing chamber system, it is conceivable that a counter is incremented by the value one when air is recognized in the concentrate line in a balancing chamber cycle and is decremented by the value one when no air is recognized in the concentrate line in a balancing chamber cycle. If the value 5 (or a different value) is, for example, exceeded or reached in this manner, an alarm is triggered and/or the special operating mode of the dialysis machine is initiated. This procedure prevents small air bubbles or unforeseen sensor fluctuations from triggering an alarm and/or initiating the special operating mode of the dialysis machine every time.

This system is not restricted to the presence of a balancing chamber system, but rather also comprises systems without a balancing chamber system.

The special operating mode can comprise a special air separation differing from normal operation and/or the flushing of the dialysis solution system or a part thereof and/or the increase of the flow rate of the dialysis solution and/or the bypass circuit of the dialyzer and optionally further measures.

The present invention relates to a dialysis machine that is equipped for receiving an extracorporeal blood system such as a blood tube set and that is equipped for receiving a dialyzer. The extracorporeal blood system and/or the dialyzer are thus not compulsory components of the machine. The invention nevertheless also comprises a dialysis machine in which the extracorporeal blood system and/or the dialyzer are inserted into the dialysis machine.

A bypass circuit of the dialyzer is to be understood such that the dialysis solution does not flow through the dialyzer, but is rather conducted past the dialyzer in a bypass line.

The flushing of the dialysis solution system or of a part thereof preferably only takes place after the special air separation. The flushing ensures that ready-to-use dialysis solution having the correct composition is present in the dialysis solution circuit when the patient is connected again and the treatment is continued.

Provision is preferably made that no air separation means, in particular no air separation chamber, is located in the concentrate line and/or between the opening of the concentrate line into the mixing region and a balancing chamber or another balancing system of the dialysis solution system.

A cost reduction can thereby be achieved. Provision is preferably made that the control unit operates the concentrate pump further so that it is necessary to wait (after the connection of a new concentrate container) until the concentrate is sucked in by the normal pump activity. To remove the air sucked in up to then and to remove the incorrectly mixed dialysis solution from the dialysis solution system, the special air separation and the flushing of the dialysis solution system, i.e. of the hydraulics or of a part thereof, are preferably carried out.

The control unit is preferably configured such that it opens and closes a valve once, or a number of times, in the operating state of the special air separation of the dialysis machine when the balancing chamber half of the balancing chamber in fluid communication with the named line is in its high-pressure phase. All the valves of the balancing chamber are closed in so doing. Air is removed from the mixing region, from the concentrate line or lines, and from the line leading to the balancing chamber by this special air separation.

The mixing region, in particular the mixing chamber, can be connected or connectable to a fresh water connector, in particular to an RO water connector.

The present invention further relates to a method of operating a dialysis machine in accordance with one of the preceding claims, wherein the conductance or a value correlated therewith is measured at two electrically conductive and mutually spaced apart elements in or at the concentrate line or lines, with the measured value being compared with a desired value, a limit value, or with a desired value range. The above statements on the dialysis machine apply accordingly to the arrangement of the electrically conductive elements.

The control unit can be formed by a single component that takes over different tasks such as the comparison of the measured value with a desired value, a limit value, or a desired value range, the initiation of the alarm, and/or the special operating mode, etc. The control unit can, however, also be formed by a plurality of separate components that take over different ones of these tasks, i.e. the control unit does not necessarily have to consist of a single component.

Provision is preferably made that if the measured value does not agree with a desired value or is not in a desired value range or exceeds or falls below a limit value, an alarm and/or a special operating mode of the dialysis machine is initiated.

As stated above, the special operating mode can comprise a special air separation differing from normal operation and/or the flushing of the dialysis solution system or a part thereof and/or the increase of the flow rate of the dialysis solution and/or the bypass circuit of the dialyzer.

It is conceivable that, in the operating state of the special air separation of the dialysis machine, the valve is opened and closed once or a multiple of times when the balancing chamber half of the balancing chamber in fluid communication with the line is in its high pressure phase to remove air from the mixing region and from the line system connected thereto. The air is expelled mechanically by the opening and closing of the valve preferably taking place a plurality of times, for example three times, such that less residual air remains in the mixing chamber that could be entrained in the next filling of the balancing chamber.

Provision can furthermore be made that the operating state of the special air separation is not selected when the measured value corresponds to a desired value or is in a desired value rang or does not exceed or fall below a specific limit value and that in this case a normal air separation is instead carried out in which the valve is preferably only opened in the dead time of the balancing chamber.

The mixing chamber or another mixing region is preferably connected to one or more concentrate lines through which concentrates move out of concentrate containers into the mixing chamber. These concentrates can, for example, be one acid concentrate and one base concentrate. The mixing chamber is typically connected to a fresh water connector, in particular to an RO water connector, such that the concentrate or concentrates can be diluted to the desired level. Reference is made to the embodiment in accordance with FIG. 1 that shows a non-restrictive example for a dialysis machine of the present invention, with the conductive elements in the concentrate lines and the control unit not being shown in FIG. 1.

The present invention is preferably used in dialysis machines that do not have an air separation apparatus.

It is pointed out at this point that the use of the term "a" or "one" also, but not necessarily, means that exactly one of the elements in question is provided, but rather also includes the plurality of elements. It must equally be pointed out that the use of the plural generally also includes one of the elements in question.

Figure 3:
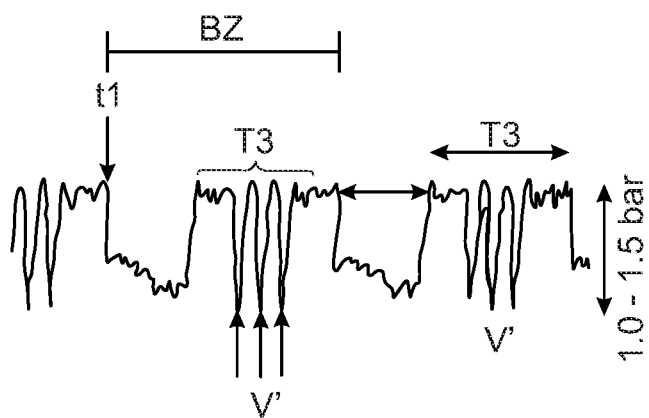
Figure 4:
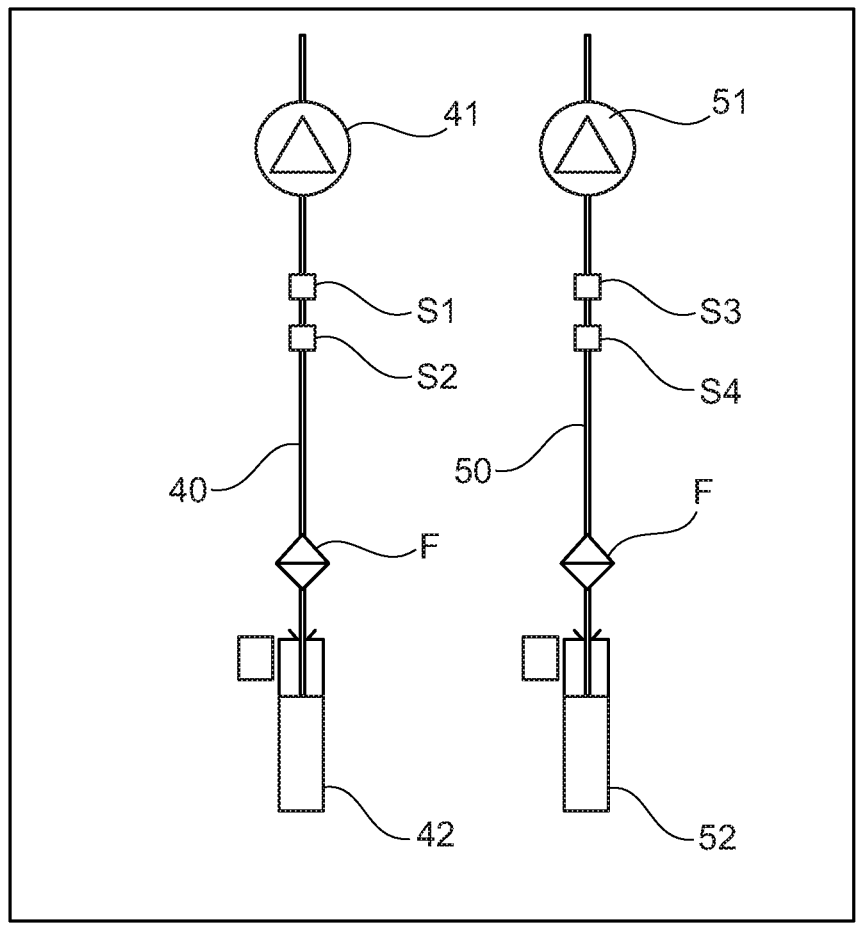

Further details and advantages of the invention will be explained in more detail with reference to an embodiment shown in the drawing. There are shown:

FIG. 1: a simplified schematic representation of the hydraulic circuit and blood circuit of a dialysis machine;

FIG. 2: the progression of the pressure over time with a normal air separation;

FIG. 3: the progression of the pressure over time with a special air separation; and FIG. 4: a simplified schematic representation of two concentrate lines of a dialysis machine in accordance with the invention.

FIG. 1 shows a hydraulic circuit and also the extracorporeal blood circuit of a dialysis machine known from the prior art. This structure can also be present identically or in a modified form in a dialysis machine in accordance with the invention so that the above statements also apply to the present invention.

FIG. 4 shows the two concentrate lines 40, 50 of which one is in fluid communication with an acid concentrate that is located in the container 42 and of which the other is in fluid communication with a base concentrate that is located in the container 52. Filters F are located in the concentrate lines downstream of the containers 42, 52. Two respective sensors in the form of electrically conductive elements S1 and S2 and S3 and S4 are located in each of the lines 40, 50 between the respective containers 42, 52 and the concentrate pumps 41, 51 that pump the concentrates into the mixing chamber.

The control unit, not shown, measures the conductances between the sensors S1 and S2, on the one hand, and between the sensors S3 and S4, on the other hand.

If in so doing a conductance is measured once or a multiple of times that is below a threshold value, an alarm is triggered and a conclusion is drawn on the presence of air in the respective line 40, 50. It is generally also covered by the invention that the conductance, etc. is measured between a sensor S1 or S2 and S3 or S4, i.e. beyond the mixing chamber.

As part of normal operation, i.e. if no air is found in the concentrate lines, the normal air separation is carried out such as has been described above and shown in FIG. 2. This air separation takes place by opening the valve V, and indeed at the dead time t1 of the balancing chamber or of the balancing chamber half filled with fresh dialysis solution, and subsequently no longer during the balancing chamber cycle BZ.

If, however, it is recognized by the conductive elements or by the control unit connected thereto that excessive air intake is taking place, which can e.g. be due to the lack of a concentrate container 42, 52 or due to its empty state, this is detected by the control unit that thereupon initiates one or more measures.

In an embodiment, the control unit initiates the following steps:

The flow rate of the dialysis solution is first increased with respect to the normal dialysis operation, e.g. to a value of 500 ml/min.

The balancing chamber halves are then interconnected by the opening of the valves such that a short-circuit takes place between the respective balancing chamber halves of the two balancing chambers or of one balancing chamber, i.e. no conveying of solution into the line L2 takes place.

Furthermore an alarm is triggered that is perceivable by the user and that e.g. indicates that the acid concentrate or the base concentrate has been used up.

A switchover is then made from the normal air separation mode in accordance with FIG. 2 to the special air separation mode in accordance with FIG. 3. This is characterized in that the valve V in accordance with FIG. 1 is opened once or preferably multiple times, e.g. three times, in the high pressure phase (T3) of the balancing chamber half filled with fresh dialysis solution. In the high pressure phase of the balancing chamber half, the latter is completely filled with liquid. This has the consequence that the opening of the valve V does not result in a flow of liquid enriched with air into the balance chamber. Air is rather removed from the mixing chamber 20 by the opening and closing of the valve so that no air or only a little air enters into the balancing chamber on the switching back into the normal operating mode or into the normal air separation mode. The probability for the occurrence of incorrect balances can thereby be avoided or at least reduced.

FIG. 3 shows the progression of the pressure over time in an arrangement in accordance with FIG. 2, wherein the same times and the same time periods are provided with the same reference symbols and it is illustrated that the valve V is opened and closed three times in the high-pressure phase T3, which is designated by the reference symbol V' and makes itself noticeable by corresponding pressure fluctuations. An opening and closing of the valve V preferably does not take place at the dead time t1.

The pressure values indicated in FIGS. 2 and 3 and all other values named as part of the present invention are of an exemplary nature and are not restrictive.

If it is found that concentrate is again present in the concentrate lines, a switchover is again made from the special air separation in accordance with FIG. 3 to the normal air separation in accordance with FIG. 2.

If the concentrate supply has been established again in that filled concentrate containers have again been connected to the concentrate lines and if air is no longer detected in the concentrate lines for a specific time period or after the end of e.g. 5 balancing chamber cycles, the flushing process is initiated.

In the flushing process, the hydraulics, i.e. the dialysis solution circuit or a part thereof, is flushed. This region can comprise the air separator of the dialysis solution circuit, filters, the balancing chamber, valves and all the lines that connect the aforesaid elements. The flushing process is carried out, for example, such that the hydraulic circuit or a part thereof is flowed through twice by ready-to-use dialysis solution.

The patient is preferably separated from the dialysis machine during the flushing process.

If the flushing process has ended, the alarm message is deleted, the dialyzate flow is again reduced to the desired value, and the patient is connected again so that the treatment can be continued.

The invention claimed is:

1. A dialysis machine that is configured to be equipped with an extracorporeal blood system comprising a dialysis solution system that is configured to be equipped with a dialyzer, wherein a mixing region, in particular a mixing chamber, is provided in which the fresh dialysis solution or a component thereof is located in the operation of the dialysis machine, with at least one concentrate line being in fluid communication with the mixing region, through which concentrate line concentrate can be conducted from a concentrate container into the mixing region, characterized in that one or more electrically conductive elements are arranged spaced apart from one another in or at the at least one concentrate line; that a measuring device is provided which is electrically connected to the conductive elements and which is configured to measure the conductance or a value correlated therewith between them; and that a control unit is provided which is configured to compare the measured value with a desired value, with a limit value, or with a desired value range, wherein the control unit is configured to initiate a special operating mode of the dialysis machine when the measured value does not agree with the desired value, exceeds or falls below a limit value, or is not in a desired value range, wherein
the special operating mode comprises a special air separation differing from normal operation and/or the flushing of the dialysis solution system or a part thereof, wherein
the flushing of the dialysis solution system or a part thereof only takes place after the special air separation.

2. A dialysis machine in accordance with claim 1, characterized in that exactly one electrically conductive element is respectively arranged in or at one concentrate line and/or that one or more concentrate lines are provided in or at which a plurality of electrically conductive elements are arranged.

3. A dialysis machine in accordance with claim 1, characterized in that the conductive elements are formed by hose connections; and/or in that the conductive elements consist of metal, preferably of stainless steel and/or titanium; and/or in that the conductive elements are arranged in or at the same concentrate line or in or at different concentrate lines.

4. A dialysis machine in accordance with claim 1, characterized in that a concentrate pump is located in the concentrate line; and in that the conductive elements are located upstream or downstream of the concentrate pump in the direction of flow of the concentrate.

5. A dialysis machine in accordance with claim 1, characterized in that the control unit is configured to initiate an alarm when the measured value does not agree with the desired value, exceeds or falls below a limit value, or is not in a desired value range.

6. A dialysis machine in accordance with claim 5, characterized in that the control unit is configured such that the alarm and/or the special operating mode of the dialysis machine is only initiated when the measured value does not agree with the desired value, exceeds or falls below a limit value, or is not in a desired value range in each case more frequently than a threshold value.

7. A dialysis machine in accordance with claim 5, characterized in that the control unit is configured such that the special operating mode comprises the increase of the flow rate of the dialysis solution and/or conducting the dialysis solution past the dialyzer in a bypass circuit of the dialyzer arranged in the dialysis solution system.

8. A dialysis machine in accordance with claim 1, characterized in that no air separation means, in particular no air separation chamber, is located in the concentrate line and/or no air separation means is located between the opening of the concentrate line into the mixing region and a balancing chamber of the dialysis solution system.

9. A dialysis machine in accordance with claim 7, characterized in that the control unit is configured such that it opens and closes a valve that is preferably in fluid communication with the mixing region once or multiple times in the operating state of the special air separation of the dialysis machine when the balancing chamber half of a balancing chamber of the dialysis solution system in fluid communication with said line is in its high pressure phase.

10. A dialysis machine in accordance with claim 1, characterized in that the mixing region, in particular the mixing chamber, is connected or connectable to a fresh water connector, in particular to an RO water connector.

11. A method of operating a dialysis machine in accordance with claim 1, characterized in that the conductance or a value correlated therewith is measured at two electrically conductive and mutually spaced apart elements in or at the concentrate line or lines; and in that the measured value is compared with a desired value, a limit value, or with a desired value range.

12. A method in accordance with claim 11, characterized in that for the case that the measured value does not agree with a desired value or is not in a desired value range or exceeds or falls below a limit value, an alarm and/or a special operating mode of the dialysis machine is initiated.

13. A method in accordance with claim 11, characterized in that the special operating mode comprises a special air separation differing from normal operation and/or the flushing of the dialysis solution system or a part thereof and/or the increase of the flow rate of the dialysis solution and/or the bypass circuit of a dialyzer arranged in the dialysis solution system.

14. A method in accordance with claim 13, characterized in that, in the operating state of the special air separation of the dialysis machine, a valve is opened and closed once or a multiple of times when the balancing chamber half of a balancing chamber of the dialysis solution system in fluid communication with the line is in its high pressure phase.

15. A method in accordance with claim 13, characterized in that the operating state of the special air separation is not selected when the measured value corresponds to a desired value or is in a desired value range or has not exceeded or fallen below a specific limit value and that in this case a normal air separation is instead carried out in which the valve is preferably only opened in the dead time of the balancing chamber of the dialysis solution system.

* * * * *